US008884044B2

(12) United States Patent
Rivas-Nass et al.

(10) Patent No.: US 8,884,044 B2
(45) Date of Patent: Nov. 11, 2014

(54) RUTHENIUM COMPLEXES HAVING (P—P)—COORDINATED DIPHOSPHORUS DONOR LIGANDS AND PROCESSES FOR PREPARING THEM

(75) Inventors: Andreas Rivas-Nass, Schriesheim (DE); Ralf Karch, Kleinostheim (DE); Roland Winde, Frankfurt (DE); Angelino Doppiu, Seligenstadt (DE); Tina Schneider, Langenselbold (DE)

(73) Assignee: Umicore AG & Co. KG, Hanau-Wolfgang (DE)

( * ) Notice: Subject to any disclaimer, the term of this patent is extended or adjusted under 35 U.S.C. 154(b) by 835 days.

(21) Appl. No.: 12/935,639

(22) PCT Filed: Mar. 26, 2009

(86) PCT No.: PCT/EP2009/002204
§ 371 (c)(1),
(2), (4) Date: Dec. 9, 2010

(87) PCT Pub. No.: WO2009/121513
PCT Pub. Date: Oct. 8, 2009

(65) Prior Publication Data
US 2011/0112318 A1 May 12, 2011

Related U.S. Application Data

(60) Provisional application No. 61/086,319, filed on Aug. 5, 2008.

(30) Foreign Application Priority Data

Apr. 1, 2008 (EP) ..................................... 08006674

(51) Int. Cl.
C07F 17/02 (2006.01)
B01J 31/24 (2006.01)
C07C 51/36 (2006.01)
C07B 53/00 (2006.01)
B01J 31/18 (2006.01)

(52) U.S. Cl.
CPC ............. C07F 17/02 (2013.01); B01J 31/2409 (2013.01); C07C 51/36 (2013.01); C07B 53/00 (2013.01); B01J 2231/645 (2013.01); B01J 2231/643 (2013.01); B01J 31/185 (2013.01); B01J 31/1865 (2013.01); B01J 2531/821 (2013.01)
USPC .................................. 556/16; 556/14; 556/15

(58) Field of Classification Search
None
See application file for complete search history.

(56) References Cited

U.S. PATENT DOCUMENTS 6,455,460 B1  9/2002  Dobbs et al.

FOREIGN PATENT DOCUMENTS

WO  2006/067412 A1  6/2006
WO  WO2006108562  10/2006
WO  WO2008138540  11/2008

OTHER PUBLICATIONS

Cavallo (J.Am.Chem.Soc., 2002, 124, 8965-8973).*
Lumini et al (Journal of Organometallic Chemistry, 1992, 434(3), 363-85).*
Consiglio et al (Journal of the Chemical Society, Chemical Communications, 1988, (1), 25-6).*
International Search Report (PCT/P2009/002204) dated Jul. 29, 2009.
A. Bauer et al—Efficient Synthesis of Ruthenium(II) n5-Dienyl Compounds Starting from Di . . . —Organometallics 2000, 19, 5471-5476.
Briel et al—Unusual Isolated Pre Catalyst Systems Using TaniaPhos MadyPhos Ligands_ Organic Reactions Catalysis Society, 2003.
C. Standfest-Hauser et al—Hydrogen-transfer catalyzed by half-sandwich Ru(II) aminophosphine complexes—J. Chem. Soc., Dalton Trans., 2001, 2989-2995.
Chiral Quest, Inc.—Technical Fact Sheet Chiral Quest Commercial Ligands and Catalysts_ Aug. 2006.
D. A. Dobbs et al—Industrielle Synthese von (+)-cis-Methyl-dihydrojasmonat . . . —Angew. Chemie 2000, 112, Nr. 11.
J. A. Wiles et al—An Alternate Route to the Active Chiral Hydrogenation Catalysts Ru(bisphosphine)(H)(solvent)3 . . . —Organometallics 2004, 23, 4564-4568.
J. B. Hoke et al—Catalytic asymmetric hydrogenation of β-ketoestersusing new BINAP complexes of ruthenium_ Journal of Organometallic Chemistry, 455 (1993) 193-196.
M. Sato et al—Synthetic studies of permethylcyclopentadinyl ruthenium(II) complexes involving dppf, . . . —Journal of Organometallic Chemistry 508 (1996) 121-127.
N. Feiken et al - 6,6-Dimethoxybiphenyl-2,2-diyl)bis(diphenylphosphine) . . . _ Organometallics 1997, 16, 537-543.
V. Rautenstrauch—New Ru(II)-Catalyzed Enantioselective Hydrogenations—Paper for —An International Symposium on Chirality—, Cambridge, UK, Sep. 5-7, 1999.

* cited by examiner

*Primary Examiner* — Sudhakar Katakam
(74) *Attorney, Agent, or Firm* — Levin Santalone LLP; John Santalone

(57) ABSTRACT

The invention relates to ruthenium complexes which have a chiral diphosphorus donor ligand and in which the ruthenium has the oxidation state (+11) and the chiral diphosphorus donor ligand has bidentate P—P coordination to the ruthenium. The ruthenium complexes are present in two forms (cationic type A and uncharged type B), are cyclic and have a four- to six-membered ring incorporating the diphosphorus donor ligand. The chiral diphosphorus donor ligands are selected from the group consisting of diphosphines, diphospholanes, diphosphites, diphosphonites and diazaphospholanes. Furthermore, processes for preparing the ruthenium complexes of types A and B, which are based on ligand exchange reactions, are described. The Ru complexes are used as catalysts for homogeneous asymmetric catalysis for preparing organic compounds.

20 Claims, No Drawings

US 8,884,044 B2

RUTHENIUM COMPLEXES HAVING (P—P)—COORDINATED DIPHOSPHORUS DONOR LIGANDS AND PROCESSES FOR PREPARING THEM

FIELD OF THE INVENTION

The present invention relates to ruthenium complexes for homogeneous catalysis, in particular P-P-coordinated cyclic ruthenium complexes having chiral diphosphorus donor ligands. The invention further provides processes for preparing them and also the use of these complexes as catalysts for homogeneous catalysis, in particular for enantioselective hydrogenation.

BACKGROUND OF THE INVENTION

Chiral diphosphorus donor ligands have been found to be valuable ligands for catalytically active metal complexes which are used in homogeneous catalysis for the enantioselective hydrogenation of organic compounds. Fields of use are the preparation of intermediates or active compounds, for example pharmaceuticals, pesticides, flavors or fragrances.

In enantioselective hydrogenation, these diphosphorus donor ligands are used together with suitable noble metal complexes.

Organometallic Ru compounds used in these hydrogenations are, for example, $[Ru(COD)Y_2]_x$, $[Ru(NBD)Y_2]_x$, $[Ru(aromatic)Y_2]_x$ or $[Ru(COD)2\text{-methyl-allyl})_2]$ (where X=2; Y=halide, COD=1,5-cyclo-octadiene, NBD=norbornadiene, aromatic=for example p-cumene or another benzene derivative).

EP 1622920B1 discloses transition metal complexes having ferrocenyldiphosphine ligands. Complexes having specific P-P coordination of the phosphine ligands are not described.

Ru complexes having (P-P)-coordinated diphosphorus donor ligands are known from the literature.

M. Sato and M. Asai (J. of Organometallic Chemistry 508 (1996) pp. 121-127) describe permethylcyclopentadienyl-Ru (II) complexes having dppf, BINAP and DIOP ligands. As a result of the permethylcyclopentadienyl radical, these complexes are very stable; use for catalytic hydrogenation is not described.

C. Standfest-Hauser, C. Slugovc et al. (J. Chem. Soc. Dalton Trans., 2001, pp. 2989-2995) report cyclic Ru(II) semisandwich complexes which likewise have a cyclopentadienyl ligand and also chelating phosphino-amine ligands. These complexes contain a cyclopentadienyl ligand ("Cp ligand") and are not very suitable for use as catalysts for homogeneous asymmetric hydrogenation. They are normally used in a specific catalysis reaction (namely transfer hydrogenation), with the Cp ligand stabilizing the catalyst and having to be coordinated to the metal during catalysis.

J. B. Hoke et al. (J. of Organomet. Chem., 1993, 455, pp. 193-196) describe ruthenium complexes in which BINAP ligands form a seven-membered ring with the Ru. The complexes contain one cyclopentadienyl group. They are very stable but display little activity in catalytic hydrogenation and some of them are unselective since the Cp ligand is bound very strongly to the metal.

P. S. Pregosin et al. (Organometallics, 1997, 16, pp. 537-543) have reported a ruthenium complex which bears the MeO-BIPHEP ligand and additionally has a cyclooctadienyl radical. The complex can be prepared only by means of a complicated process and is very air- and moisture-sensitive. Use for catalytic hydrogenation is not described. A similar complex bearing the BINAP ligand has been described by S. H. Bergens et al. (Organometallics, 2004, 23, pp. 4564-4568). An acetonitrile complex was isolated in the synthesis and this is not very active in catalysis.

A. Salzer et al. (Organometallics, 2000, 19, pp. 5471-5476) have reported the preparation of a seven-membered BINAP-ruthenium complex from a (bispentadienyl)Ru compound as starting complex.

D. A. Dobbs et al. (Angew. Chem. 2000, volume 112, pp. 2080-2083) describe a ruthenium-containing precatalyst having a P—P-coordinated DuPhos ligand. The cyclic compound is an Ru hybrid species and has an uncharged cyclooctatrienyl ligand. It is very sensitive and was prepared in a glove box (inert gas: Ar containing <1 ppm of oxygen). Such sensitive compounds are not very suitable for industrial use.

WO 00/37478 describes transition metal complexes which have a metal atom of transition group 7 or 8 and in which both P atoms of a diphosphine ligand are simultaneously coordinated to the central atom, but the complexes are neither isolated nor characterized. No preparative method is described; rather, the complexes are generated by combining the ligands and the appropriate transition metal salts in the reaction solvent shortly before use ("in-situ"). These in-situ processes are prior art. Few studies have hitherto been carried out on the structure of the metal complexes generated in-situ; the corresponding complexes were not isolated but instead used directly in the reaction mixture for homogeneous catalysis, in particular for catalytic hydrogenation. The mechanistic studies are carried out using model systems which do not correspond to the real active catalytic species.

U.S. Pat. No. 6,455,460 describes a ruthenium catalyst obtainable by a process which comprises putting together an appropriate Ru(II) complex, a chelating diphosphine and an acid comprising an non-coordinating anion. The reaction is performed under an oxygen-free atmosphere.

Disadvantages of the catalytic hydrogenation processes described hitherto and the catalysts used therein are, in particular, the low reactivity, the low enantioselectivities and a high consumption of noble metal-containing catalyst, i.e. a low "substrate/catalyst" (S/C) ratio. Furthermore, long hydrogenation times are required. In addition, many of the complexes described are difficult to synthesize, are air-sensitive and are not very suitable for industrial use.

SUMMARY OF THE INVENTION

It was therefore an object of the present invention to provide improved catalysts for homogeneous, asymmetric hydrogenation which overcome the abovementioned disadvantages. A further object was to provide suitable processes for preparing the catalysts of the invention. In particular, these processes should be able to be used in industry and be environmentally friendly and inexpensive.

This object is achieved by the provision of the ruthenium complexes of the types A and B as claimed in claim 1 of the invention. Furthermore, processes for preparing the inventive complexes of types A and B are provided in claims 12 and 22. Preferred embodiments of the complexes and the processes are described in the respective dependent claims.

The present invention describes ruthenium complexes having a chiral diphosphorus donor ligand of the P(1)-P(2) type for homogeneous catalysis. The complexes are of two different types (type A and type B), with the ruthenium having the oxidation state +II and the diphosphorus donor ligands displaying bidentate P-P coordination to the Ru. The ruthenium complexes of the invention are cyclic and together with the diphosphorus donor ligand have a four- to six-membered ring.

DETAILED DESCRIPTION OF THE PREFERRED EMBODIMENTS

In the search for well-defined Ru complexes having these chiral diphosphorus donor ligands, it has surprisingly been found that simultaneous coordination of both P atoms of the diphosphorus donor ligands to a central Ru atom can be achieved under particular conditions. This gives cyclic Ru complexes which have a four- to six-membered ring in their structure and display very good catalytic activity in homogeneous catalysis.

The effect of P-P coordination is obtained by use of diphosphorus donor ligands P(1)-P(2) which are sterically able to form a four- to six-membered ring with the central Ru atom. For the purposes of the present patent application, Ru complexes bearing ferrocenylphosphine ligands having phosphine groups on the different Cp rings have a six-membered ring. The ferrocene unit P—C—Fe—C—P makes available five ring atoms of the ring formed. The numbering of the ring members used here is shown schematically in figure 1.

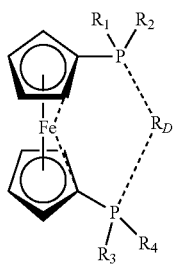

FIG. 1

The chiral diphosphorus donor ligand P(1)-P(2) is generally selected from the group consisting of diphosphines, diphospholanes, diphosphites, diphosphonites and diazaphospholanes.

Examples of suitable diphosphorus donor ligands for preparing four-membered cyclic Ru complexes are the ligands of the MiniPhos and Trichickenfootphos families.

Examples of suitable diphosphorus donor ligands for preparing five-membered cyclic Ru complexes are the ligands of the families DIPAMP, Norphos, PROPHOS, DuPHOS, Chiraphos, Bis-P* family, DepyPhos (or DeguPhos), RoPhos, CATAXIUM, ButiPhane, (1,2-ethylene)-BinaPhane, (1,2-phenylene)-BinaPhane, Binapine, TangPhos, BPE, BasPhos, MalPhos, Me-KetalPhos, Helmchen ligands, PennPhos, UCAP, Hoge ligands and CNR-Phos. However, the use range of the invention is not restricted to these ligands.

Examples of suitable diphosphorus donor ligands for preparing six-membered cyclic Ru complexes are the ligands of the families BDPP (or SKEWPHOS), BPPFOH, MandyPhos, JosiPhos, FerroTANE Me-f-KetalPhos, Ferrocelane, Trifer and (1,1'-ferrocene)-BinaPhane. However, the use range of the invention is not restricted to these ligands.

A preferred embodiment of the invention comprises ruthenium complexes having five- or six-membered rings. Preferred ligand systems are the ligands of the DepyPhos (Deguphos) family which form five-membered rings and the Josiphos and Mandyphos ligands which lead to six-membered rings.

The diphosphorus donor ligands indicated above can have axial, central and/or planar chirality and are in most cases commercially available. When these ligands are used in the preparative process of the invention, cyclic Ru complexes having a four- to six-membered ring in their structure are obtained. However, other chiral diphosphorus donor ligands are also suitable, as long as they make formation of a four- to six-membered ring possible.

The present invention further provides a process for preparing the inventive ruthenium complexes of the types A and B, in which specific Ru starting compounds are reacted with a chiral diphosphorus donor ligand or the ruthenium complex of type A is reacted with a further ligand.

The effect of P-P coordination in the ruthenium complexes of the invention is achieved in the present preparative process by use of a specific Ru starting compound in which the central Ru atom is in the oxidation state +II and which has at least three uncharged ligands $L_D$.

It has the following general formula $$[Z—Ru-(L_D)_n]^+ E^-$$

wherein
Ru is in the oxidation state +II,
n is an integer obeying n≥3,
$L_D$ is an uncharged ligand,
Z is a π-bonded anionic open pentadienyl ligand and
$E^-$ is the anion of an oxo acid or complex acid.

The at least three uncharged ligands $L_D$ belong to the class of 2-electron donor ligands, for example secondary or tertiary phosphines (ligands of the $PR_2H$ or $PR_3$ type, for example triphenylphosphine) or N-heterocyclic carbene ligands (known as NHC ligands). The ligands $L_D$ are preferably weakly bound to the central Ru atom. At least two of these ligands are replaced in the reaction with a chiral diphosphorus donor ligand. Examples of suitable ligands $L_D$ are ligands from the group consisting of nitriles, isonitriles, alcohols, ethers, amines, acid amides, lactams and sulfones; for example acetonitrile ($CH_3CN$), diethyl ether (DEE), water ($H_2O$) or acetone. It is also possible to use cyclic ligands such as tetrahydrofuran (THF), dioxane, pyridine, imidazole or thiophene. Mixed systems comprising different types of ligands are also possible. However, solvent ligands from the group consisting of acetonitrile ($CH_3CN$), diethyl ether, water and acetone are preferred.

Furthermore, the Ru starting compound has a π-bonded anionic (i.e. singly negatively charged) ligand Z. Ligands Z encompass open (i.e. acyclic) pentadienyl ligands. Such ligands can be substituted or unsubstituted. They have a delocalized π-electron system. The substituted pentadienyl ligands can be monosubstituted, disubstituted or trisubstituted.

Preferred substituted pentadienyl ligands Z are 1-methylpentadienyl, 2-methylpentadienyl, 3-phenylpentadienyl, 2,4-dimethylpentadienyl or 2,3,4-trimethylpentadienyl.

Closed, cyclic aromatic π-systems such as substituted or unsubstituted cyclopentadienyl ligands are not suitable as ligands Z. It has been found that such cyclopentadienyl ligands are bound very strongly to the central Ru atom because of the high electron density of the aromatic π-electron system present. This hinders access of reactants during the catalysis reaction, for example in a catalytic hydrogenation. Thus, for example, the coordination of the compound to be hydrogenated to the Ru atom is made difficult in a hydrogenation reaction, as a result of which the corresponding Ru complex has a low reactivity as catalyst.

The Ru starting compound used for the process of the invention is present in the form of a cation having a single positive charge and has, as further constituent, E⁻ (the anion of an oxo acid or complex acid) as counterion. Examples of anions E⁻ are $HSO_4^-$, $CF_3SO_3^-$, $ClO_4^-$, $CF_3COO^-$, $CH_3COO^-$, $BF_4^-$, $B(aryl)_4^-$, $SbF_6^-$ or $PF_6^-$.

Examples of suitable Ru starting compounds are [Ru(2,4-dimethylpentadienyl) $(CH_3CN)_3$]⁺$BF_4^-$, [Ru(2,4-dimethylpentadienyl) $(H_2O)_3$]⁺$BF_4^-$ and [Ru(2,4-dimethylpentadienyl) $(acetone)_3$]⁺$BF_4^-$. The Ru starting compound can firstly be prepared from known, commercially available Ru precursor compounds (e.g. bis(η5-(2,4-dimethylpentadienyl)Ru) by reaction with the appropriate ligand $L_D$ according to process steps known from the literature.

It has been found that the reaction of the above-described Ru starting compound with the suitable chiral diphosphorus donor ligands (hereinafter referred to as P(1)-P(2) for short) gives the Ru complexes of the invention. The formation of the complex of type A occurs by ligand exchange in the preparative process according to eq. (1):

Equation (1)

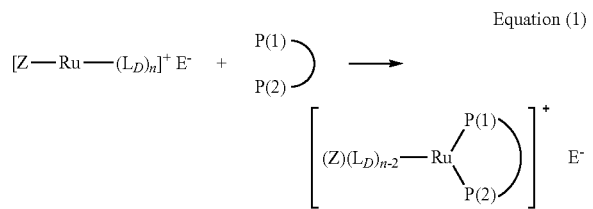

The inventive Ru complex of type A is obtained according to eq. (1). This complex is cationic, i.e. singly positively charged. In the preparation of the complex, the chiral diphosphorus donor ligand is reacted with the above-described Ru starting compound, with at least two of the ligands $L_D$ being replaced in the reaction. If the Ru starting compound has more than two ligands $L_D$, the remaining ligands $L_D$ stay coordinated to the ruthenium. They can be replaced or eliminated in a subsequent step. This gives the inventive Ru complex of type B.

The preparation of the Ru complexes of types A and B is preferably carried out under a protective gas atmosphere using the Schlenk technique and oxygen-free solvents. However, this is not necessary in all cases.

To prepare type A, the diphosphorus donor ligands are typically reacted with the Ru starting compound in a suitable solvent at temperatures in the range from −80° C. to 80° C., preferably in the range from 20 to 60° C. and particularly preferably at room temperature (25° C.), while stirring.

Suitable solvents are chlorinated hydrocarbons such as chloroform, methylene chloride, trichloroethane or dichloroethane. However, preference is given to using dipolar, aprotic solvents such as acetone, THF or dioxane. The reaction times are in the range from 1 hour to 48 hours, preferably in the range from 1 hour to 24 hours. It can be advantageous to use the ligand in a small excess in the preparation of the Ru complexes of type A, with the excess being able to be in the range from 1 to 10 mol-% (based on the Ru starting compound). The subsequent isolation, washing and purification steps are well known to those skilled in the art. To remove solvent residues, the complexes are dried under reduced pressure.

The present invention further provides Ru complexes of type B. These complexes are overall electrically neutral and have a negatively charged ligand $L_z$ in addition to the P-P-coordinated chiral diphosphorus donor ligand, the π-bonded anionic pentadienyl ligand Z and, if present, the ligand $L_D$.

This ligand $L_z$ is introduced by replacement of one of the ligands $L_D$ by an anion, preferably a halide ion (fluoride, chloride, bromide or iodide) or a pseudohalide ion (e.g. CN⁻, SCN⁻, cyanate, isocyanate, etc.).

The Ru complex of type B is preferably prepared from the complex of type A by ligand exchange, for example by replacement of an acetonitrile molecule by iodide (cf. example 2). Equation (2) describes the replacement of the ligand $L_D$ by a negatively charged ligand $L_z$:

Equation (2)

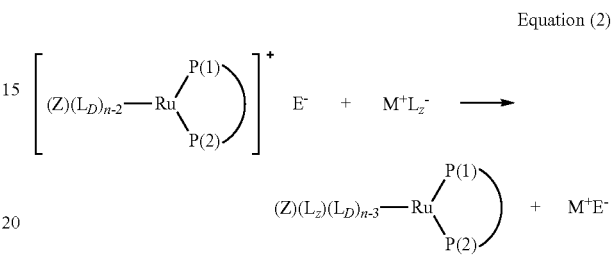

To carry out the reaction according to equation (2), the cationic Ru complex (type A) is reacted in suitable solvents such as chlorinated hydrocarbons (e.g. chloroform, methylene, chloride, trichloroethane or dichloroethane), alcohols, ketones (e.g. acetone) or cyclic ethers (e.g. THF or dioxane). However, preference is given to using aqueous solvent mixtures, in particular a mixture of a dipolar, aprotic solvent with deionized water. Here, the cationic Ru complex (type A) is, for example, dissolved in acetone/water (2:1) and reacted with the ligand $L_z$ at temperatures in the range from 0° to 50° C. The ligand $L_z$ is preferably added in the form of a salt $M^+L_z$ for example in the form of an alkali metal halide or ammonium halide. The product generally precipitates and can be separated off.

The aqueous solvent mixtures are particularly suitable for industrial syntheses for reasons of environmental protection and occupational hygiene. It has surprisingly been found that the chlorinated hydrocarbons used hitherto can be replaced as solvents without decreases in yield.

The inventive Ru complexes of type A

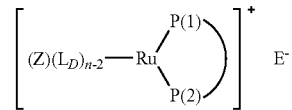

and of type B

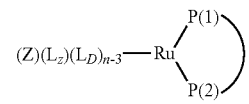

where in each case
Ru is present in the oxidation state +II,
P(1)-P(2) is a chiral diphosphorus donor ligand,
n is an integer which obeys n≥3,
$L_D$ is at least one uncharged ligand,
Z is a π-bonded anionic open pentadienyl ligand,
E⁻ is an anion of an oxo acid or complex acid and
$L_z$ is at least one anionic ligand, and the chiral diphosphorus donor ligand P(1)-P(2) has bidentate P-P coordination and forms a four- to six-membered ring with the ruthenium, are effective homogeneous catalysts for the asymmetric hydrogenation of prochiral organic compounds.

A shared characteristic of the inventive Ru complexes of types A and B is the presence of the anionic open pentadienyl ligand in the complex. It has surprisingly been found that this gives a higher reactivity of the Ru complexes in catalysis, in particular in asymmetric hydrogenation. The open pentadienyl ligand is presumably easier to destabilize than closed ligand systems such as cyclopentadienyl and cyclooctadienyl, so that it can make available a coordination site for the substrate molecule to be hydrogenated. It has surprisingly been found that the ligands $L_D$ and/or $L_z$ also play a very important role. They presumably block a coordination site so that the substrate can coordinate to the metal only in a particular way, as a result of which the enantioselectivity is increased.

The inventive Ru complexes of types A and B are therefore used as catalysts for homogeneous asymmetric catalysis, for example for the enantioselective hydrogenation of multiple bonds. For the purposes of the present invention, multiple bonds are double bonds between a carbon atom and a further carbon atom (C═C) or oxygen atom (C═O) or nitrogen atom (C═N).

Furthermore, the ruthenium complexes of the invention can also be used as catalysts for other asymmetric reactions. These include C—C, C—O, C—N, C—P, C—Si, C—B or C-halogen coupling reactions. Examples are asymmetric cyclization reactions, asymmetric oligomerizations and asymmetric polymerization reactions.

The inventive ruthenium(II) complexes of types A and B are used as defined compounds. In comparison, Ru complexes which are used together with the diphosphorus donor ligands in in-situ processes display poorer catalytic properties.

The following examples illustrate the invention without restricting its scope.

EXAMPLES

Example 1

Preparation of (η5-2,4-Dimethylpentadienyl) (CH$_3$CN)-(Josiphos-SL-J212-1) Ruthenium(II) Tetrafluoroborate a) Preparation of (η4-2,4-dimethylpentadiene-η2-C, H) (η5-2,4-dimethylpentadienyl) ruthenium tetrafluoroborate In a 100 ml Schlenk tube provided with a magnetic stirrer, 1.1 g (3.77 mmol) of bis(η5-2,4-dimethylpentadienyl) ruthenium (UMICORE, Hanau) are dissolved in 50 ml of diethyl ether. 0.51 ml (3.77 mmol) of a 54% strength HBF$_4$-Et$_2$O solution (from Aldrich) is added dropwise at room temperature over a period of 10 minutes. After the addition is complete, the mixture is allowed to settle and the completeness of precipitation is tested by addition of a further drop of HBF$_4$-Et$_2$O. The supernatant solvent is taken off and the solid is washed twice with diethyl ether. The light-yellow residue is dried under reduced pressure. Yield: 1.43 g (100%).

b) Preparation of the Acetonitrile Complex (η5-2,4-dimethylpentadienyl) (CH$_3$CN)$_3$ruthenium(II) Tetrafluoroborate (Starting Compound)

0.41 g (1.1 mmol) of (η4-2,4-dimethylpentadiene-η2-C, H) (η5-2,4-dimethylpentadienyl) ruthenium tetrafluoroborate prepared in step a) are admixed with 10 ml of acetonitrile. The orange solution is stirred for 10 minutes and the solvent is removed under reduced pressure to give an orange solid. Yield: 0.44 g (100%).

c) Preparation of (η5-2,4-Dimethylpentadienyl) (CH$_3$CN)-(Josiphos SL J212-1) Ruthenium (II) Tetrafluoroborate In a 50 ml round-bottomed flask provided with a magnetic stirrer, the acetonitrile complex (η5-2,4-dimethylpentadienyl) (CH$_3$CN)$_3$ruthenium(II) tetrafluoroborate is dissolved in 15 ml of methylene chloride and stirred with 200 mg (0.38 mmol) of Josiphos SL-J212-1 (from Solvias, Basle, CH) at room temperature for 6 hours. 50 ml of n-hexane are then added dropwise to the solution. A red-orange solid precipitates and is filtered off. The residual solvent is removed at room temperature under reduced pressure. This gives a product as a mixture of three diastereomers, yield: 95%. The P-P coordination of the ligand (and thus the presence of a 6-membered ring) is demonstrated by the $^{31}$P NMR spectrum.

Characterization:
$^{31}$P NMR (CD$_2$C$_2$) δ: 10.32 ppm (d, $J_{PP}$=28.5 Hz), 11.80 ppm (d, $J_{PP}$=31.0 Hz), 20.10 ppm (d, $J_{PP}$=29.8 Hz), 75.79 ppm (d, $J_{PP}$=31.0 Hz), 89.55 ppm (d, $J_{PP}$=28.5 Hz), 94.75 ppm (d, $J_{PP}$=29.8 Hz).

d) Use for Catalytic Hydrogenation

The (η5-2,4-dimethylpentadienyl) (CH$_3$CN) (Josiphos-SL-J212-1) ruthenium(II) tetrafluoroborate complex prepared as described in example 1 is used for the asymmetric hydrogenation of E-2-methyl-2-butenoic acid. The hydrogenation is carried out in an autoclave under 50 bar of hydrogen; solvent: methanol, temperature: 50° C. After a reaction time of 20 hours, the hydrogen pressure is removed. The complex according to the invention gives very good results when used as catalyst for enantioselective catalytic hydrogenation.

Example 2

Preparation of (η5-2,4-Dimethylpentadienyl) (iodo)-(Josiphos-SL-J212-1) Ruthenium(II)

In a 25 ml round-bottomed flask provided with a magnetic stirrer, the acetonitrile complex (η5-2,4-dimethylpentadienyl) (SL-J212-1) (CH$_3$CN)ruthenium(II) tetrafluoroborate prepared as described in example 1b) (150 mg, 0.18 mmol) is dissolved in 4 ml of acetone and 2 ml of water and stirred with lithium iodide (LiI, 28.5 mg, 0.21 mmol) at room temperature for 3 hours. The solution is evaporated to dryness at room temperature under reduced pressure. The residue is washed three times with 1 ml of water. This gives the product in the form of a diastereomerically pure compound. Yield: 90%. The P-P coordination of the SL-J-212-1 is demonstrated by the $^{31}$P-NMR spectrum.

Characterization:
$^{31}$P NMR (CD$_2$C$_2$) δ: 7.51 ppm (d, $J_{PP}$=35.9 Hz), 84.30 ppm (d, $J_{PP}$=35.9 Hz).

Use for Catalytic Hydrogenation:
The (Josiphos SL-J-212-1)(iodo)ruthenium(II) complex prepared as described in example 2 is used for the asymmetric hydrogenation of E-2-methyl-2-butenoic acid. The complex gives very good results as catalyst for enantioselective catalytic hydrogenation.

Example 3

Preparation of (η5-2,4-Dimethylpentadienyl) (CH$_3$CN)-((R,R)-DepyPhos) Ruthenium(II) Tetrafluoroborate In a 50 ml Schlenk tube provided with a magnetic stirrer, the acetonitrile complex (η5-2,4-dimethylpentadienyl) (CH$_3$CN)$_3$ruthenium (II) tetrafluoroborate prepared as described in example 1b) is dissolved in 15 ml of methylene chloride and stirred with 25 mg (0.05 mmol) of (R,R) DepyPhos (from Digital Speciality Chemicals, Toronto, Canada) at room temperature for half an hour. 50 ml of n-hexane are then added dropwise to the solution. A yellow-orange solid precipitates and is filtered off. The residual solvent is removed at room temperature under reduced pressure. The product is obtained in the form of a diastereomerically pure compound, yield: 98%. The P-P coordination of the ligand (and thus the presence of a 5-membered ring) is demonstrated by the $^{31}$P NMR spectrum.

Use for Catalytic Hydrogenation:

The complex prepared as described in example 3 is used for the asymmetric hydrogenation of E-2-methyl-2-butenoic acid. The hydrogenation is carried out in an autoclave under 50 bar of hydrogen; solvent: methanol, temperature: 50° C. After a reaction time of 20 hours, the hydrogen pressure is removed. The complex gives very good results as catalyst for enantioselective catalytic hydrogenation.

What is claimed is:

1. A ruthenium complex having a chiral diphosphorus donor ligand for homogeneous catalysis having the general formula

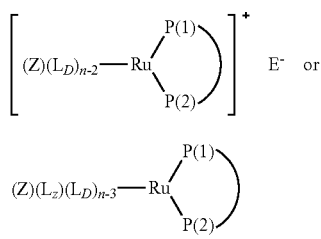

(type A) or (type B)

wherein
ruthenium is present in the oxidation state +II,
P(1)-P(2) is a chiral diphosphorus donor ligand,
n is an integer which obeys n≥3,
L$_D$ is at least one uncharged 2-electron donor ligand and is a solvent ligand from the group consisting of acetonitrile (CH$_3$CN), diethyl ether, water, acetone, tetrahydrofuran, dioxane, pyridine, imidazole and thiophene,
Z is a π-bonded anionic open, acyclic pentadienyl ligand,
E$^-$ is an anion of an oxo acid or complex acid and
L$_z$ is at least one anionic ligand,
and the chiral diphosphorus donor ligand P(1)-P(2) has bidentate P-P coordination and forms a four- to six-membered ring with the ruthenium.

2. The ruthenium complex as claimed in claim 1, wherein the chiral diphosphorus donor ligand P(1)-P(2) is selected from the group consisting of diphosphines, diphospholanes, diphosphites, diphosphonites and diazaphospholanes.

3. The ruthenium complex as claimed in claim 1, wherein a four-membered ring is present and the chiral diphosphorus donor ligand P(1)-P(2) is selected from the group consisting of MiniPhos and Trichickenfootphos ligands.

4. The ruthenium complex as claimed in claim 1, wherein a five-membered ring is present and the chiral diphosphorus donor ligand P(1)-P(2) is selected from the group consisting of DIPAMP, Norphos, PROPHOS, DuPHOS, Chiraphos, Bis-P* family, DepyPhos (or DeguPhos), RoPhos, CATAXIUM, ButiPhane, (1,2-ethylene)-BinaPhane, (1,2-phenylene)-BinaPhane, Binapine, TangPhos, BPE, BasPhos, MalPhos, Me-KetalPhos, Helmchen ligands, PennPhos, UCAP, Hoge ligands and CNR-Phos ligands.

5. The ruthenium complex as claimed in claim 1, wherein a six-membered ring is present and the chiral diphosphorus donor ligand P(1)-P(2) is selected from the group consisting of BDPP (or SKEWPHOS), BPPFOH, MandyPhos, JosiPhos, FerroTANE Me-f-KetalPhos, Ferrocelane, Trifer and (1,1'-ferrocene)-BinaPhane ligands.

6. The ruthenium complex as claimed in claim 1, wherein Z is a substituted open pentadienyl ligand and is 1-methylpentadienyl, 2,4-dimethylpentadienyl or 2,3,4-trimethylpentadienyl.

7. The ruthenium complex as claimed in claim 1, wherein Z is 2,4-dimethylpentadienyl.

8. The ruthenium complex as claimed in claim 1, wherein E$^-$ is an anion from the group consisting of HSO$_4^-$, CF$_3$SO$_3^-$, CF$_3$CO$_2^-$, CH$_3$CO$_2^-$, ClO$_4^-$, BF$_4^-$, B(aryl)$_4^-$, SbF$_6^-$ or PF$_6^-$.

9. The ruthenium complex as claimed in claim 1, wherein L$_z$ is at least one anionic ligand from the group consisting of halides and pseudohalides.

10. The ruthenium complex as claimed in claim 1, wherein L$_z$ is iodide, Z is 2,4-dimethylpentadienyl and E$^-$ is BF$_4^-$.

11. A process for preparing the ruthenium complex (type A) as claimed in claim 1, wherein an Ru starting compound of the general formula

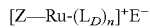

wherein
Ru is in the oxidation state +II
n is an integer obeying n≥3,
L$_D$ is at least one uncharged 2-electron donor ligand and is a solvent ligand from the group consisting of acetonitrile (CH$_3$CN), diethyl ether, water, acetone, tetrahydrofuran, dioxane, pyridine, imidazole and thiophene,
Z is a π-bonded anionic open, acyclic pentadienyl ligand and
E$^-$ is an anion of an oxo acid or complex acid,
is reacted with a chiral diphosphorus donor ligand P(1)-P(2), wherein the chiral diphosphorus donor ligand P(1)-P(2) forms a four- to six-membered ring with the ruthenium.

12. The process as claimed in claim 11, wherein the chiral diphosphorus donor ligand P(1)-P(2) is selected from the group consisting of diphosphines, diphospholanes, diphosphites, diphosphonites and diazaphospholanes.

13. The process as claimed in claim 11, wherein the chiral diphosphorus donor ligand P(1)-P(2) forms a four-membered ring with the ruthenium and is selected from the group consisting of MiniPhos and Trichickenfootphos ligands.

14. The process as claimed in claim 11, wherein the chiral diphosphorus donor ligand P(1)-P(2) forms a five-membered ring with the ruthenium and is selected from the group consisting of DIPAMP, Norphos, PROPHOS, DuPHOS, Chiraphos, Bis-P* family, DepyPhos (or DeguPhos), RoPhos, CATAXIUM, ButiPhane, (1,2-ethylene)-BinaPhane, (1,2-phenylene)-BinaPhane, Binapine, TangPhos, BPE, BasPhos, MalPhos, Me-KetalPhos, Helmchen ligands, PennPhos, UCAP, Hoge ligands and CNR-Phos ligands.

15. The process as claimed in claim 11, wherein the chiral diphosphorus donor ligand P(1)-P(2) forms a six-membered ring with the ruthenium and is selected from the group consisting of BDPP (or SKEWPHOS), BPPFOH, MandyPhos, JosiPhos, FerroTANE Me-f-KetalPhos, Ferrocelane, Trifer and (1,1'-ferrocene)-BinaPhane ligands.

16. The process as claimed in claim 11, wherein Z is 1-methylpentadienyl, 2,4-dimethylpentadienyl or 2,3,4-trimethylpentadienyl.

17. The process as claimed in claim 11, wherein $E^-$ is an anion from the group consisting of $HSO_4^-$, $CF_3SO_3^-$, $CF_3CO_2^-$, $CH_3CO_2^-$, $ClO_4^-$, $BF_4^-$, $B(aryl)_4^-$, $SbF_6^-$ or $PF_6^-$.

18. The process as claimed in claim 11, wherein dipolar, aprotic solvents such as acetone, THF or dioxane are used as solvents.

19. A process for preparing the ruthenium complex (type B) as claimed in claim 1, wherein the cationic ruthenium complex of type A is reacted with a negatively charged ligand $L_z$ from the group consisting of halides and pseudohalides.

20. The process as claimed in claim 19, wherein an aqueous solvent mixture, in particular a mixture of a dipolar, aprotic solvent with water, is used as solvent.

* * * * *